United States Patent
Matsumoto et al.

(10) Patent No.: US 6,709,856 B2
(45) Date of Patent: Mar. 23, 2004

(54) LIQUID SAMPLE MEASURING DEVICE CONTAINING ELECTRODE SENSOR WITH ENZYME LAYER

(75) Inventors: Toru Matsumoto, Tokyo (JP); Hiroshi Kohashi, Tokyo (JP); Yasuyoshi Matsumoto, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/818,803

(22) Filed: Mar. 27, 2001

(65) Prior Publication Data

US 2001/0035349 A1 Nov. 1, 2001

(30) Foreign Application Priority Data

Mar. 28, 2000 (JP) .......................................... 2000-088792

(51) Int. Cl.[7] .............................. C12M 1/34; C12Q 1/00; C12N 11/14; C12N 11/02
(52) U.S. Cl. .................... 435/287.1; 435/4; 435/176; 435/177; 435/817
(58) Field of Search .............................. 435/4, 176, 177, 435/180, 182, 817, 287.1

(56) References Cited

FOREIGN PATENT DOCUMENTS

| JP | 58-110849 | 7/1983 |
|----|-----------|--------|
| JP | 58-155081 | 9/1983 |
| JP | JU-61-167554 | 10/1986 |
| JP | 63-181860 | 11/1988 |
| JP | JU-117761 | 8/1989 |
| JP | 4-3347 | 1/1992 |
| JP | 6-273372 | 9/1994 |
| JP | 7-325088 | 12/1995 |
| JP | 8-114539 | 5/1996 |
| JP | 9-196920 | 7/1997 |
| JP | 10-339716 | 12/1998 |
| JP | 2000-081409 | 3/2000 |
| JP | 2000-081410 | 3/2000 |

Primary Examiner—David M. Naff
(74) Attorney, Agent, or Firm—Scully, Scott, Murphy & Presser

(57) ABSTRACT

A device and method are provided using a sensor containing an electrode with an enzyme layer to determine a component in a liquid sample. Inlet and outlet channels feed liquid sample to and from the sensor surface. The inlet channel is placed an angle of preferably 1 to 80 degrees to the sensor surface, and an inlet channel end opening is at a distance from the sensor surface of preferably two fold or less of an inlet channel inner diameter. The angle and distance provide good measurement accuracy, stable measurement sensitivity and rapid response. The sensor may be vertically sandwiched between upper and lower parts, and be removable from the upper part. Liquid sample is continuously moved from the inlet channel over the sensor surface and discharged through the outlet channel. Liquid sample speed over the sensor surface is adjusted to provide sensor output in proportion to concentration of the liquid.

17 Claims, 11 Drawing Sheets

Fig. 3(a)
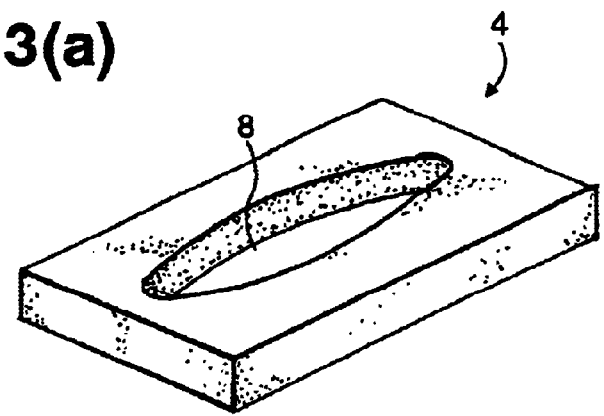
Fig. 3(b)
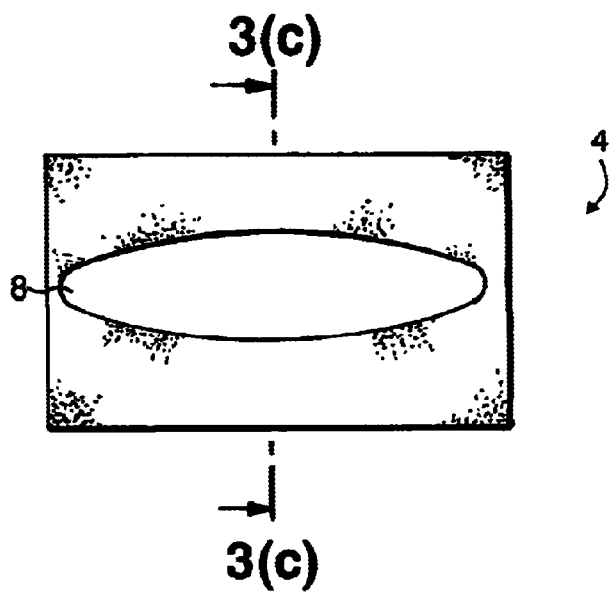
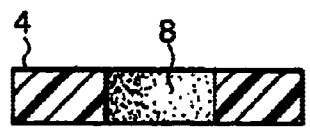
Fig. 3(c)

LIQUID SAMPLE MEASURING DEVICE CONTAINING ELECTRODE SENSOR WITH ENZYME LAYER

BACKGROUND OF THE INVENTION

1. Field of the Invention

This invention relates to a measuring device for a liquid sample and a method for measuring the liquid sample, where a sensor comprising an enzyme layer is used to determine a particular component contained in a liquid sample introduced from a liquid sample inlet channel.

2. Description of the Prior Art

For measuring a component in a liquid sample such as blood and case fluid, there has been widely employed an approach that a collected liquid sample such as blood and case fluid is directly introduced into a sensor unit, it is measured with the sensor and then the liquid sample is discharged. In such a measuring procedure, a particular component is measured during the liquid sample as a continuous flow passes over the sensor surface.

JP-A 10-339716 has disclosed an example of such a measuring device for a liquid sample. FIG. 10 shows the structure of the device. This device consists of a case 48, a sensor platform 47, a measuring circuit 61, a data processor 62 and a data display 63. The case 48 comprises a standard liquid inlet 41, a standard liquid outlet 42, a sample inlet 44 and a sample outlet 43. The sensor platform 47 consists of a screw 45, a stopper 49, a sensor 46, and two liquid inlet channels 50a and 50b. The stopper 49 and the sensor 46 are fixed on the platform 47 with the screw 45. A signal detected by the sensor 46 is transmitted via an electric cable 53 through the measuring circuit 61, the data processor 62 and finally to the data display 62 where the signal is displayed as a measured value. The sensor platform 47 and the case 48 are placed in a manner that they are mutually slidable.

The sensor 46 in the liquid inlet channels 50a and 50b is removably fixed inside of the liquid inlet channel 50a by the sensor platform 47. Here, the sensor is fixed such that the exposed surface of the sensor 46 to the liquid inlet channel 50a is placed in the substantially same plane as, preferably slightly inner than, the inner surface of the liquid inlet channel 50a. Thus, in the liquid inlet channel 50a, a standard or sample liquid may not be disturbed or remain and therefore may be quickly charged and discharged.

The above prior art have advantages that a small amount of liquid sample may be measured and that since a sensor unit is removable, a worn sensor may be replaced with a new one. Furthermore, despite a simple structure, such a device may achieve good measurement accuracy. However, a measuring device with a simple structure has been recently required to achieve performance comparable to a larger device, and there is a room for improving measurement accuracy and stability in a measured value.

In a device measuring a liquid sample by introducing it to a sensor unit via a channel, particularly a device measuring a liquid sample as a continuous flow during it passes over the sensor surface, the sensor is generally placed on the side wall of the channel so that the liquid sample flows in parallel to a plane containing the sensor surface. The above-mentioned application has disclosed an example of a device having such a configuration.

However, when a sensor has an enzyme layer in the upper part of its electrode in a device having such a configuration, it may cause reduced measurement accuracy, unstable measured value and reduced response.

In a sensor comprising an enzyme layer, a component to be measured is diffused in the enzyme layer and is subject to an enzyme reaction in the enzyme layer to generate a current in an electrode which gives a measured value. In such a sensor, the amount of a chemical species derived from the component to be measured which reaches the electrode depends on a concentration of the component to be measured near the sensor surface. However, when the liquid sample moves to a direction parallel to the sensor surface, the concentration of the component to be measured may tend to vary near the sensor surface, leading to reduced measurement accuracy and unstable measured value.

When placing the sensor on the side wall of the channel, it is difficult to place the sensor such that its surface is in the completely same plane as that of the inner wall of the channel. Resultantly, a slight misalignment may lead to protrusion or depression of the sensor surface. Such a shape may cause disturbance of liquid sample flow near the sensor surface where the concentration of the component to be measured may, thus, vary, leading to reduced measurement accuracy and unstable measured value. Furthermore, in a second measurement after the first measurement and washing, a dead space which may be formed near the sensor may frequently cause reduced measurement accuracy, unstable measured value and reduced response due to residual measured liquid sample or washing. In particular, when using a biological fluid as a liquid sample, the amount of the sample is so small that a dead space formed may give significant influence. In this respect, the above-mentioned JP-A 10-339716 has descried that protrusion or depression of a sensor surface may reduce measurement sensitivity.

In addition, in a measuring device where a sensor is removable from its installation site, its structure may cause misalignment of the sensor surface to the inner wall of the channel. Furthermore, whenever replacing a sensor, precise alignment is required so that sensor replacement becomes difficult work. Thus, problems due to misalignment between the inner wall of the channel and the sensor surface becomes more prominent for a measuring device in which a sensor is removable.

On the other hand, for example, the inner structure of the channel may be improved for solving the above problems. However, such an improvement may lead to a complex device structure, thus make sensor replacement difficult and make mass production or cost reduction of the device difficult.

In addition, in a measuring device according to the prior art, a measured value may become unstable when measuring a biological fluid as a liquid sample repeatedly or continuously, which may be due to adhesion of contaminants such as proteins contained in the biological fluid on the inner wall of the channel. In a measuring device according to the prior art, there is also a room for improvement in this respect.

In view of the above problems, an object of this invention is to provide a device with an enzyme layer for measuring a liquid sample and a method for measuring the liquid sample, which may achieve excellent measurement accuracy, stable measurement sensitivity and quick response as well as prevention of sensitivity reduction in repeated or continuous measurement. In particular, an objective of this invention is to solve the above problems in a measuring device in which a sensor unit is removable.

SUMMARY OF THE INVENTION

This invention provides a device for measuring a liquid sample comprising:
- a sensor for measuring a component in the liquid sample;
- a liquid sample inlet channel for feeding the liquid sample to the sensor surface; and
- a liquid sample outlet channel for discharging the liquid sample from the sensor surface,
- the sensor having an electrode and an enzyme layer in the upper part of the electrode,
- the liquid sample inlet channel being placed at an angle to the sensor surface, and one opening end of the liquid sample inlet channel being placed in the vicinity of the sensor surface.

As described above, in a conventional measuring device generally having a style that a sensor is mounted on the side wall of a channel, there has been problems of, for example, reduced measurement accuracy, unstable measured value and reduced response when using a sensor comprising an enzyme layer. To solve the problem, this invention employs a configuration that a liquid sample inlet channel is placed at an angle to a sensor surface and one opening end of the liquid sample inlet channel is placed in the vicinity of the sensor surface, whereby a flow condition of the liquid sample suitable to measurement near the sensor surface may be achieved, resulting in excellent measurement accuracy, stable measurement sensitivity and quick response. Even when the liquid sample inlet channel is placed at an angle to the sensor surface, if one opening end of the liquid sample inlet channel is too distant from the sensor surface, the above effect may not be adequately achieved because the flow condition of the liquid sample is not necessarily good near the sensor surface. In this invention, the distance between the opening end and the sensor surface is, for example, two fold or less of the inner diameter of the liquid sample inlet channel, preferably equal to or less than the inner diameter of the liquid sample inlet channel.

In this invention, a configuration where the liquid sample inlet channel is placed at an angle to the sensor surface may further improve the flow condition near the sensor surface to significantly improve measurement accuracy and measured-value stability.

This invention also provides a device for measuring a liquid sample comprising a sensor for measuring a component in the liquid sample and an upper and a lower cases vertically sandwiching the sensor, where the upper case comprises a liquid sample inlet channel for feeding the liquid sample to the sensor surface and a liquid sample outlet channel for discharging the liquid sample from the sensor surface, the sensor comprising an electrode and an enzyme layer in the upper part of the electrode and being removable from the upper case, the liquid sample inlet channel being placed at an angle to the sensor surface and one opening end of the liquid sample inlet channel being placed in the vicinity of the sensor surface.

In the device of this invention, since the sensor is removable from the upper case, a worn sensor may be quickly replaced. Furthermore, the inside of the device may be cleaned after removing the sensor. Since the sensor, the upper case and the lower case may be separately manufactured, the upper and the lower cases may be produced from a plastic material in a large scale by, for example, injection molding and degree of freedom may be increased in designing a shape of the sensor. For example, a layout of the electrode in the sensor may be freely changed.

In a measuring device in which a sensor is removable from an upper case, a sensor surface may be generally misaligned to the inner wall of a liquid sample inlet or outlet channel (hereinafter, referred to as a "channel" as appropriate). Furthermore, whenever replacing a sensor, precise alignment is required, leading to reduced workability. Since removing a worn sensor and mounting a new sensor are usually conducted manually by a user of the measuring device on site, controlling the problem is an important technical subject.

To solve the problem, in this invention the liquid sample inlet channel is placed at an angle to the sensor surface while one opening end of the liquid sample inlet channel is placed in the vicinity of the sensor surface, so that a flow state near the sensor surface becomes suitable to measurement and influence of misalignment may be relatively reduced. Small misalignment of the sensor may, therefore, cause the minimum reduction in measurement accuracy and measured-value stability.

As described above, since the liquid sample measuring device according to this invention has a removable sensor unit, it may not only provide a variety of advantages but also effectively resolve the problem prominently caused when employing the above configuration, i.e., misalignment of the sensor surface to the inner wall of the channel.

Additionally, the above device for measuring a liquid sample may have a configuration that an elastic member having an opening is placed between the upper case and the sensor surface; the opening interconnects between the liquid sample inlet channel and the sensor, and between the liquid sample outlet channel and the sensor; and a part of the sensor surface is in contact with the liquid sample via the opening. Such a configuration may provide the following effects.

First, it may prevent a dead space from being formed between the upper case and the sensor, leading to good measurement accuracy, stable measured value and good response. Adequate measurement accuracy may be achieved even with a small amount of sample.

When a case with a channel is directly in contact with the sensor surface, it may often cause a gap between the case and the sensor surface. Such a gap may disturb the flow condition of the liquid sample over the sensor surface, leading to reduced measurement accuracy, unstable measured value and reduced response. Although an adhesive may be used to prevent such a gap, it may integrate the sensor with the case and therefore, a configuration with a removable sensor unit may not be provided. On the other hand, in this invention, an elastic member is placed between the sensor and the upper case. The elastic member having proper elasticity can prevent a gap from being formed between the upper case and the sensor and therefore may prevent disturbance of the flow condition of the liquid sample over the sensor surface. Consequently, a good flow condition of the liquid sample may be achieved, resulting in good measurement accuracy, stable measured value and good response.

Second, it may prevent leakage between the upper case and the sensor. As described above, the elastic member in this invention has proper elasticity so that it may prevent a gap between the upper case and the sensor, resulting in effective prevention of leakage of the liquid sample.

Third, it may significantly reduce effects of misalignment during mounting the sensor on the case.

In this invention, a part of the sensor surface is in contact with a liquid sample via an opening. Specifically, the opening defines a part of the sensor surface to be in contact with the liquid sample, and plays a role of a guide for introducing the liquid sample to a given area on the sensor surface. It may, therefore, prevent the problem that misalignment during mounting the sensor on the case causes protrusion of the sensor in the channel or that the liquid sample is in contact with the side wall of the sensor. Since the position of the sensor may be made stable to the channel, the flow condition of the liquid sample near the sensor surface becomes stable, resulting in improved measurement accuracy, measured-value stability and response.

This invention also provides a method for measuring a liquid sample wherein using a device for measuring a liquid sample comprising a sensor having an electrode and an enzyme layer in the upper part of the electrode, a liquid sample inlet channel for feeding the liquid sample to the sensor surface and a liquid sample outlet channel for discharging the liquid sample from the sensor surface, a component in the liquid sample is measured while continuously moving the liquid sample fed from the liquid sample inlet channel over the sensor surface, a moving speed of the liquid sample being adjusted to provide a sensor output in proportion to a concentration of the liquid sample.

In the method for measuring a liquid sample where a component in the liquid sample is measured while continuously moving the liquid sample over the sensor surface, measurement accuracy and measured-value stability may significantly vary depending on a moving speed of the liquid sample. Taking it into account in the method for measuring a liquid sample, a moving speed of the liquid sample is adjusted to provide accurate and stable measurement results. Specifically, the speed is adjusted to provide a sensor output in proportion to a concentration of a component to be determined. According to the method for measuring a liquid sample of this invention, employing the above adjusting procedure may provide good measurement accuracy and stable measured value.

BRIEF DESCRIPTION OF THE DRAWINGS

FIGS. 3(a)–3(c) show a structure of the elastic member used in the device for measuring a liquid sample in FIG. 1.

DETAILED DESCRIPTION OF PREFERRED EMBODIMENTS

A device for measuring a liquid sample according to this invention having the above particular configuration may stabilize flow condition of the liquid sample near the sensor surface to prevent a dead space from being formed. Thus, the structure is suitable for measuring a component in the liquid sample while continuously moving the liquid sample fed from a liquid sample inlet channel over the sensor surface.

Figure 15:
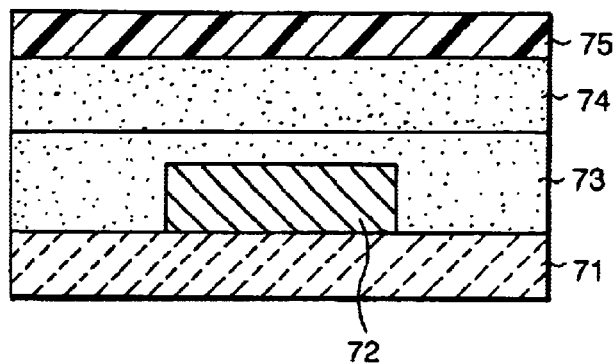
FIG. 15 is a cross section of an enzyme sensor.

A sensor used in a device for measuring a liquid sample of this invention has a configuration as shown in, for example, FIG. 15. The sensor in the figure comprises a working electrode 72 on a substrate 71, on which a binding layer 73, an immobilized enzyme layer 74 and a permeation restricting layer 75 are sequentially formed. The substrate 71 may be made of quartz. The working electrode may be made of, for example, platinum. The binding layer 73 is formed for improving adhesiveness of the working electrode 72 to the immobilized enzyme layer 74, which may be made of a silane coupling agent.

A permeation restricting layer 75 permeates a liquid sample in a restricting manner and may be made of, for example, a fluoroalcohol polycarboxylate.

The immobilized enzyme layer 74 is a layer in which an enzyme selected depending on a component to be measured is immobilized, and comprises an organic polymer base material in which a catalytic enzyme is immobilized. The immobilized enzyme layer 74 may be formed by, for example, adding dropwise and applying by spin coating a solution containing some kind of enzyme, a protein cross-linking agent such as glutaraldehyde and albumin. Albumin may protect the enzyme from a reaction with the cross-linking agent and may be a protein base material. There are no restrictions to a process for forming the immobilized enzyme layer 74 as long as the layer can be formed with an even film thickness, and in addition to spin coating, screen printing may be used.

Enzymes to be immobilized include lactate oxidase, glucose oxidase, urate oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyruvate oxidase. These enzymes may be used alone or simultaneously in combination of two or more.

In this invention, a liquid sample inlet channel is placed at an angle to a sensor surface. Specifically, the channel is positioned such that the central axis of the liquid sample inlet channel is oblique to a plane containing the sensor surface. An angle of the liquid sample inlet channel to the sensor surface may be appropriately selected depending on various factors such as the type of the sensor, the type of the liquid sample and a method of using the device, but a lower limit is preferably 1 degree, more preferably 10 degree, most preferably 20 degree, while an upper limit is preferably 80 degree, more preferably 70 degree, most preferably 60 degree. An angle within the above range may improve measurement accuracy and measured-value stability and accelerate sensor response. Furthermore, since influence of misalignment between the sensor and the channel is minimized, it may reduce dispersion in sensor properties due to skill of mounting the sensor.

In this invention, a liquid sample outlet channel may be placed at an angle to a sensor surface and one opening end of the liquid sample outlet channel is placed in the vicinity of the sensor surface. In such a configuration, flow condition of the liquid sample over the sensor surface may be further stabilized, resulting in better measurement accuracy, measured-value stability and response. An angle of the liquid sample outlet channel to the sensor surface may be appropriately selected depending on various factors such as the type of the sensor, the type of the liquid sample and a method of using the device, but a lower limit is preferably 1 degree, more preferably 10 degree, while an upper limit is preferably 80 degree, more preferably 70 degree, most preferably 60 degree. An angle within the above range may further improve measurement accuracy and measured-value stability and accelerate sensor response. Furthermore, since influence of misalignment between the sensor and the channel is minimized, it may reduce dispersion in sensor properties due to skill of mounting the sensor. The liquid sample inlet and outlet channels to the sensor surface may be the same or different.

In this invention, an angle formed by the liquid sample inlet and outlet channels when viewing from a direction vertical to a plane containing the sensor surface may be, for example, 90 degree to 180 degree both inclusive. The angle within the range may allow the liquid sample to be smoothly moved from the liquid sample inlet channel to the liquid sample outlet channel, resulting in stable measurement. It may be suitable to form the liquid sample inlet and outlet channels in the substantially same plane for achieving further smooth movement of the liquid sample.

In this invention, when an elastic member is placed between the upper case and the sensor, the liquid sample moves through the liquid sample inlet channel, the opening, the sensor and the liquid sample outlet channel in sequence. The elastic member may be preferably made of a material with proper elasticity. It may prevent a gap from being formed between the upper case and the sensor surface so that reduction of measurement accuracy due to formation of a dead space and leakage of the liquid sample may be prevented. The elastic member is preferably made of a material with good waterproof property, which may effectively prevent leakage of the liquid sample. Therefore, materials which may be preferably used include silicone resins and fluororesins.

The elastic member is preferably a film. A thickness of the elastic member may be appropriately selected, taking some relevant factors such as the material into consideration. When using a silicone resin or fluororesin, its thickness is preferably 0.1 $\mu$m to 1 mm. An excessively thick film may cause unstable flow condition over the sensor surface while an excessively thin film may lead to insufficient elasticity so that a gap may be generated between the upper case and the sensor surface.

The elastic member may have usually one opening or optionally have two or more openings.

In this invention, the opening ends of the liquid sample inlet and outlet channels may be separate or common. A common opening end may allow the liquid sample to smoothly move from the liquid sample inlet channel to the liquid sample outlet channel, leading to stable measurement.

Figure 17A:
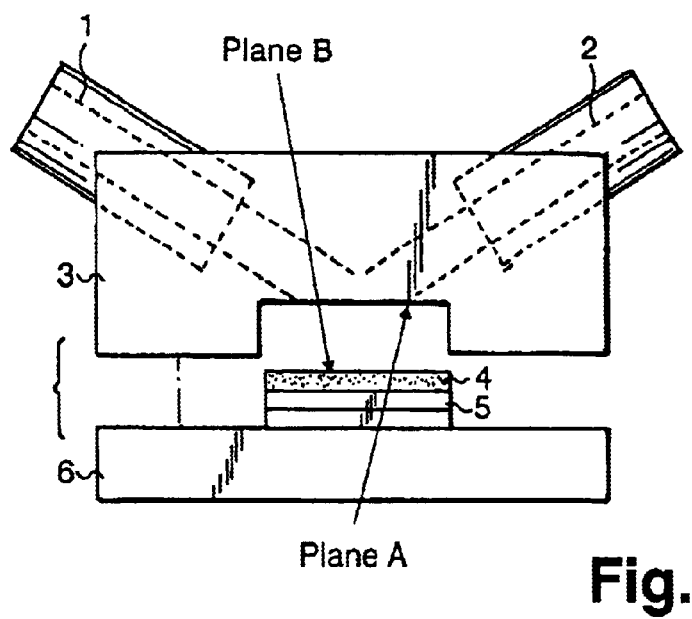
FIGS. 17(a)–17(b) show positional relationship between an elastic member opening and an opening end of a channel in a device for measuring a liquid sample according to this invention.
Figure 17B:
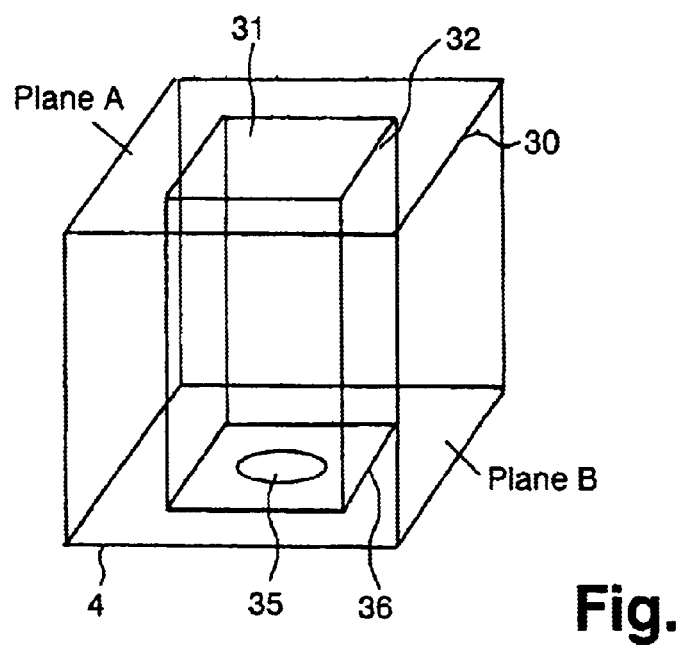

When forming a common opening end, it is preferable that in a plane in which the upper case is in contact with the elastic member (Planes A and B in the FIG. 17), the periphery of the common opening end is outer from that of the opening in the elastic member. FIG. 17 shows positional relationship between the opening 35 in the elastic member 4 and the common opening end 31 formed in the lower surface 30 of the upper case (a plane in contact with the elastic member 4). In the structure shown in this figure, the periphery 32 of the common opening end 31 is outer from the periphery 36 of the opening 35 in the elastic member 4. It may prevent a dead space to be formed between the upper case 3 and the elastic member 4 and allow the opening 35 to certainly act as a guide for introducing the liquid sample to a given region over the sensor surface 5. As a result, it may lead to further improvement in measurement accuracy, measured-value stability and response.

An elastic member in this invention is removable to the upper case or the sensor. The one side or both sides of the elastic member may be treated with an adhesive for improving handling property during mounting the sensor.

The upper and the lower cases may be mutually fixed using a screw, but a hook may be used in place of a screw.

A device for measuring a liquid sample according to this invention may have a plurality of sensors, whereby multiple particular components in the liquid sample may be simultaneously measured. Each sensor may have an elastic member or one elastic member having a single opening may be provided for a plurality of sensors.

In this invention, there may be single or multiple liquid sample inlet and outlet channels, respectively. A combination of single channels for both inlet and outlet may make movement of the liquid sample smooth and manufacturing easier. When a plurality of liquid sample inlet or outlet channels are formed, there may be one or more elastic members.

A liquid sample in this invention may be any liquid. For example, liquid on an epithelium such as a skin or mucosa from an organism including human may be used as a liquid sample. Examples of a sample may include sweat, blood, suction effusion fluid. Examples of a component in a liquid sample to be measured include glucose, lactic acid, uric acid, cholesterols and choline.

In this invention, an antifouling layer may be formed on the inner surface of the liquid sample inlet or outlet channel. A "antifouling layer" as used herein refers to a layer which can prevent a component in a liquid sample from adhering to a channel or sensor. For example, when using a biological fluid as a liquid sample, there may be a problem of reduced sensitivity due to adhesion of a component such as proteins to a channel and/or a sensor. An antifouling layer may be formed to solve such a problem. The antifouling layer preferably comprises a fluoroalcohol ester of a polycarboxylic acid. This polymer has a vinyl polymer without fluorine atoms as a principal chain and —COOH radical as a side chain so that it exhibits good adherence to the liquid sample inlet channel, the liquid sample outlet channel and the elastic member to give an antifouling layer which is unlikely damaged even after long-term use. Its antifouling effect may be owing to inhibition of physico-chemical adhesion because a fluoroalcohol ester of a polycarboxylic acid hardly reacts with contaminants such as proteins and urea compounds. Forming such an antifouling layer may allow the liquid sample to smoothly move in the channel and make cleaning of the sensor easier.

A molecular weight of a polymer constituting an antifouling layer is preferably 1000 to 50000, more preferably 3000 to 20000. An excessively large molecular weight may make solution preparation difficult while an excessively small molecular weight provides an unsatisfactory antifouling layer. A molecular weight as used herein refers to a number average molecular weight, i.e., a molecular weight determined by GPC (gel permeation chromatography).

A device for measuring a liquid sample according to this invention may be manufactured, for example, as follows. First, a material such as a plastic with a lower cost which may be produced in a large scale is used to prepare an upper case having a liquid sample inlet channel and a liquid sample outlet channel as well as a lower case for fixing a sensor. Separately, a sensor is prepared. Each layer constituting the sensor may be formed by an appropriate technique such as spin coating and dipping. Then, the sensor, the upper case and the lower case are assembled with, for example, screws to prepare the main part of the device for measuring a liquid sample of this invention. When forming an antifouling layer in the inner surface of the channel or of the opening in the elastic member, the inside of, e.g., the channel (all the area to be in contact with the liquid) may be contacted with a solution of a material for the antifouling layer before mounting the sensor, and then dried. For example, the antifouling layer may be formed by dipping an upper case with channels into a solution of a material for the antifouling layer or by injecting a solution of a material for the antifouling layer into the inside of the channel using a syringe to form the antifouling layer.

Embodiment 1

Figure 1A:
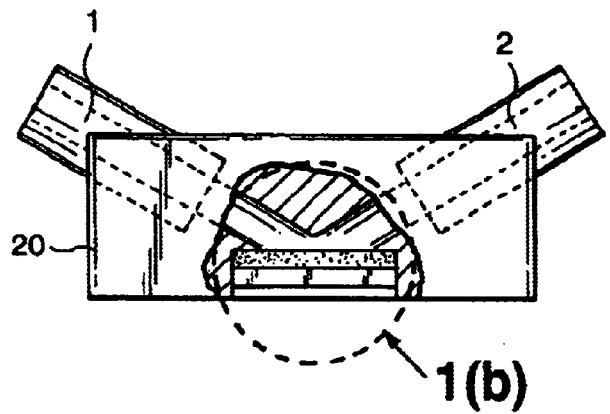
FIGS. 1(a)–1(c) show an example of a device for measuring a liquid sample according to this invention.
Figure 1B:
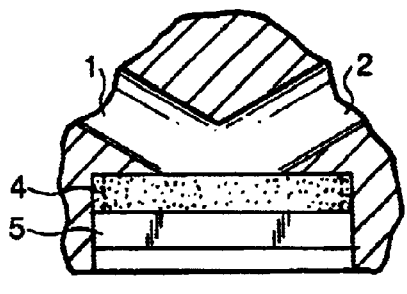
Figure 1C:
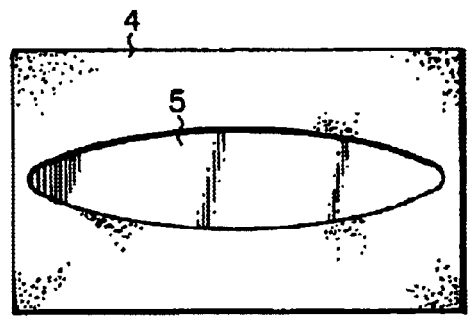
Figure 2:
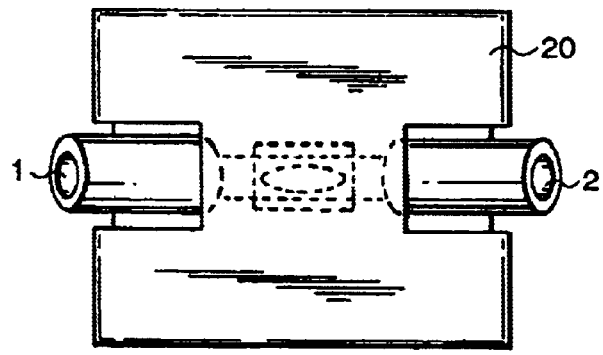
FIG. 2 shows an example of a device for measuring a liquid sample according to this invention.

The first embodiment of this invention will be described with reference to FIGS. 1 to 3. A device for measuring a liquid sample of this embodiment comprises, as shown in FIG. 1, a sensor 5 allowing a particular component in a liquid sample to be measured, a case 20 and an elastic member 4 lying between them. The case 20 comprises a liquid sample inlet channel 1 for feeding the liquid sample and a liquid sample outlet channel 2 for discharging the liquid sample. The elastic member 4 has waterproof property and is disposed such that it is in closely contact with the sensor 5, the liquid sample inlet channel 1 and the liquid sample outlet channel 2. The elastic member 4 has an opening with an appropriate shape acting as a channel.

There are no restrictions to the shapes of cross-section and the lengths for the liquid sample inlet channel 1 and the liquid sample outlet channel 2 as long as smooth feeding, retention and flowing of the liquid sample can be ensured, but linear channels with a circular cross section in which a dead volume is reduced as much as possible are preferable. Herein, an angle formed by the liquid sample inlet and outlet channels 1,2 when viewing from a direction vertical to a plane containing the sensor surface may be, for example, 90° to 180° both inclusive. The angle within the range may allow the liquid sample to be smoothly moved from the liquid sample inlet channel 1 to the liquid sample outlet channel 2, resulting in stable measurement. It may be particularly suitable to form the liquid sample inlet and outlet channels in the substantially same plane for achieving further smooth movement of the liquid sample. The device for measuring a liquid sample of this invention has such a configuration, and as shown in FIG. 2, viewing from the top side, the liquid sample inlet and outlet channels 1, 2 are aligned on a straight line.

Angles of the liquid sample inlet and outlet channels 1, 2 to the surface of the sensor may have any value as long as these can be connected with the elastic member 4, preferably at least 1°, more preferably at least 10°, most preferably at least 20°. The upper limit is preferably 80°, more preferably 70°, most preferably 60°. When these angles are 0°, the liquid sample inlet channel 1, the liquid sample outlet channel 2 and the elastic member 4 are substantially in the same plane so that the elastic member cannot be in closely contact with the liquid sample inlet channel 1 or the liquid sample outlet channel 2 and thus waterproof may not be achieved, resulting in tendency to leakage. Although the angles formed by the liquid sample inlet and outlet channels 1, 2 may not necessarily have the same value, they are preferably the same because smooth flowing of the liquid sample can be ensured.

The sensor 5 may be, but not limited to, an amperometric or potentiometric detection type of electrochemical sensor, specifically a sensor capable of detecting an electrode active material or ion generated by an enzyme catalytic reaction. An amperometric detection type of enzyme sensor may be a sensor capable of detecting, for example, glucose, lactic acid, uric acid, cholesterols and choline. A potentiometric-detection, ion-sensitive, field-effect type of transistor may detect ion components such as hydrogen, sodium, potassium and chlorine ions. It is not necessary to dispose electrodes such as a reference electrode and a counter electrode other than a working electrode used as an electrode of the sensor 5 within the sensor 5. For example, they may be mounted in the liquid sample inlet channel 1 or the liquid sample outlet channel 2.

The structure of the elastic member 4 will be described with reference to FIG. 3. The elastic member 4 has an opening 8. A liquid sample from the liquid sample inlet channel 1 flows through the opening 8 while a particular component is detected over the surface of the sensor 5, and then passes through the liquid sample outlet channel 2 to be discharged. There are no restrictions to the size of the opening 8 as long as smooth flow of the liquid sample is not blocked, but at least it is preferably equal to or larger than the inner diameter of the liquid sample inlet channel 1 or the inner diameter of the liquid sample outlet channel 2. The size of the opening 8 may be smaller than that of the common opening end of the liquid sample inlet and outlet channels 1, 2 and the periphery of the common opening end may be outside of the periphery of the opening 8 of the elastic member 4 so that generation of a dead space may be prevented between the case 20 and the elastic member 4 and the opening may certainly act as a guide for feeding the liquid sample into a given area over the surface of the sensor 5, resulting in further improvement in measurement accuracy, measured-value stability and response. The opening 8 is designed to be smaller than the whole surface of the sensor 5 so that a part of the sensor surface may be in contact with the liquid sample via the opening 8.

The elastic member 4 is removable to the upper case 4, the liquid sample inlet channel 1, the liquid sample outlet channel 2 and the sensor 5. The one side or both sides of the elastic member is treated with an adhesive for improving handling property during mounting. The elastic member 4 is herein mainly made of a silicone resin for improving adherence to the liquid sample inlet and outlet channels 1, 2, i.e., waterproof property, but there are no restrictions to its material as long as it can prevent leakage from a gap between the liquid sample inlet and outlet channels 1, 2 and the elastic member 4. Thus, the elastic member 4 is mounted between the sensor 5 and the liquid sample inlet and outlet channels 1, 2, and the opening 8 is formed inside of the elastic member 4 to further prevent leakage of the liquid sample.

The elastic member 4 and the sensor 5 may be fixed by applying an adhesive to the liquid sample inlet and outlet channels 1, 2, the case 20 and both sides of the elastic member 4 or by gumming up the sensor 5 and the case 20 with an adhesive.

Embodiment 2

Figure 4A:
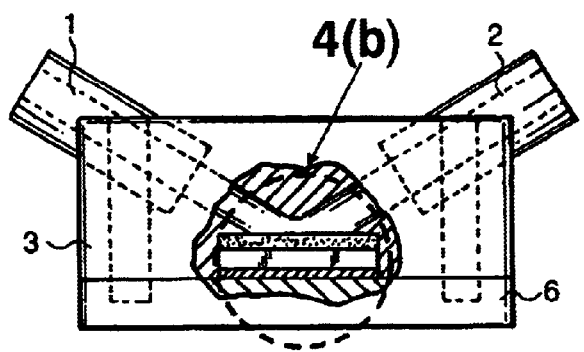
FIGS. 4(a)–4(c) show an example of a device for measuring a liquid sample according to this invention.
Figure 4B:
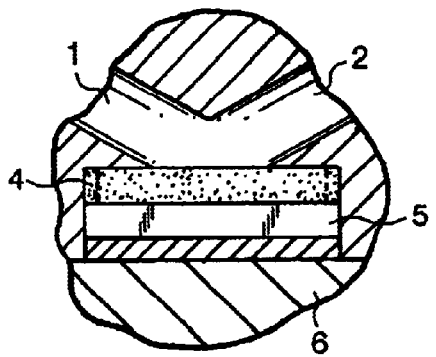
Figure 4C:
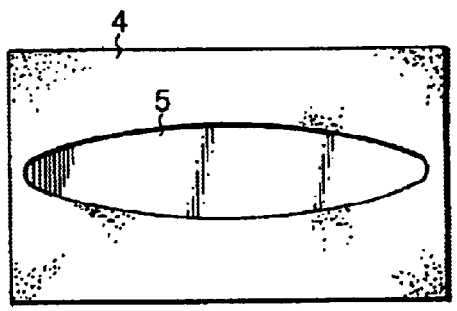

A device for measuring a liquid sample according to this invention will be described with reference to FIGS. 4 to 6 and 16. A device for measuring a liquid sample of this embodiment comprises, as shown in FIG. 4, a sensor 5 allowing a particular component in a liquid sample to be measured, an upper case 3 and a lower case 6 sandwiching the sensor, and an elastic member 4 lying between the upper case 3 and the sensor 5. The upper and the lower cases 3, 6 are assembled with a screw 7. The upper case 3 comprises a liquid sample inlet channel 1 for feeding the liquid sample and a liquid sample outlet channel 2 for discharging the liquid sample. The elastic member 4 has waterproof property and is disposed such that it is in closely contact with the sensor 5, the liquid sample inlet channel 1 and the liquid sample outlet channel 2. The elastic member 4 has an opening with an appropriate shape acting as a channel.

Figure 5:
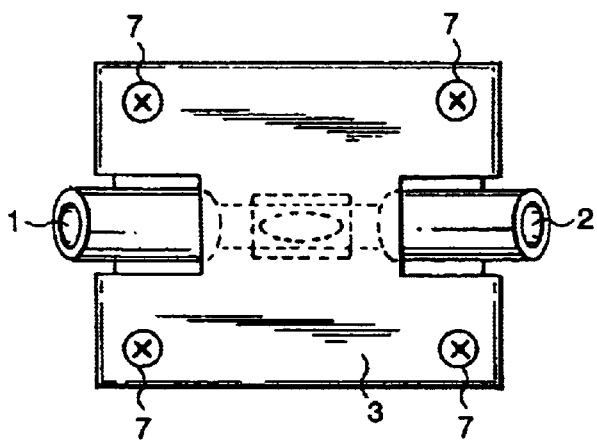
FIG. 5 shows an example of a device for measuring a liquid sample according to this invention.

Assembling using the screw 7 as shown in FIG. 5 is preferable for facilitating replacement of the sensor 5, but an assembling method is not limited to the method using the screw 7 as long as the sensor can be replaced. There are no restrictions to the number of the screw 7 as long as the sensor 5 and the elastic member 4 are firmly mounted on the lower case 6.

Figure 6:
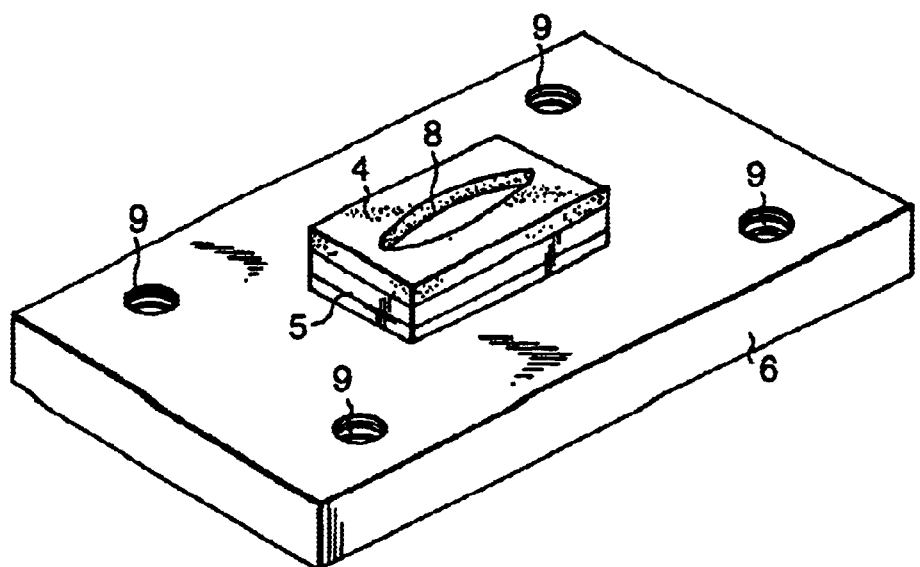
FIG. 6 shows a part of a device for measuring a liquid sample in FIG. 4 in detail.

FIG. 6 shows the lower case 6 before being assembled with the upper case 3, where the sensor 5 and the elastic member 4 are sequentially formed on the lower case 6. The lower case 6 may be mounted to the upper case 3 by fixing the upper case 3 and the screw hole 9 with the screw 7 while pressing the lower case 6 shown in FIG. 6 onto the bottom surface of the upper case 3. Thus, replacement or mounting of the sensor 5 is quite easy.

Figure 16:
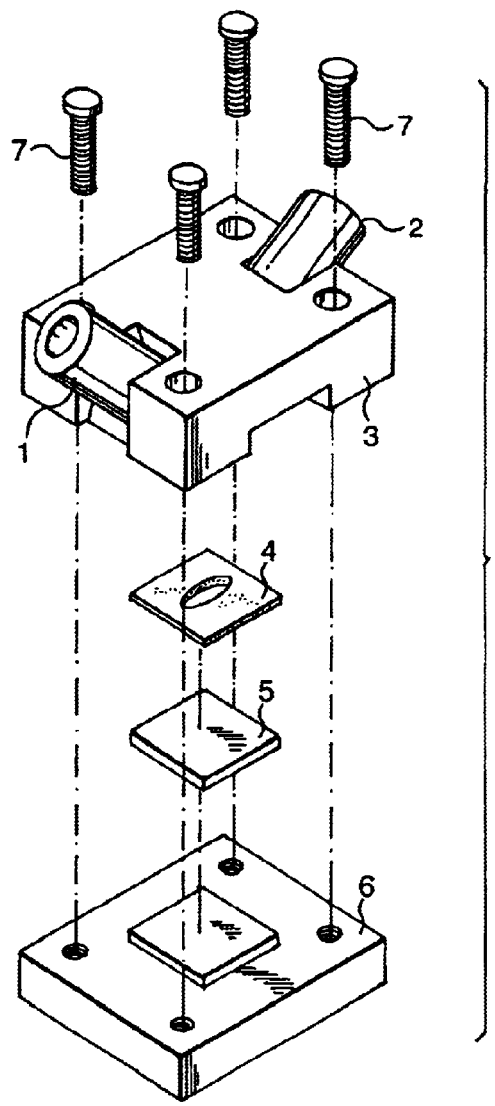
FIG. 16 shows an example of a device for measuring a liquid sample according to this invention.

FIG. 16 is a perspective view for more understanding of the device for measuring a liquid sample illustrated in FIGS. 4 and 5. It can be seen from the figure that the device for measuring a liquid sample of this embodiment may be easily disassembled and that replacement or mounting of the sensor 5 is quite easy.

Embodiment 3

Figure 7:
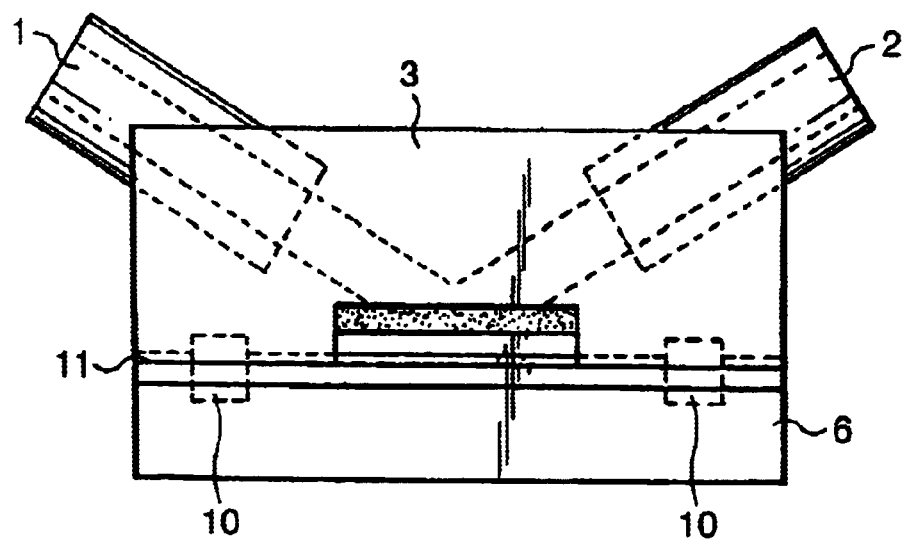
FIG. 7 shows an example of a device for measuring a liquid sample according to this invention.

In a device for measuring a liquid sample of this embodiment, an upper case 3 and a lower case 6 are, as shown in FIG. 7, assembled with a hook 10. By this assembling method, the whole bottom surfaces of the upper case 3 and the lower case 6 evenly adhere together because the hook 5 is held by a hook (10)-holding groove 11 formed in the upper case 3 to fix the sensor 5 (not shown), leading to a lower manufacturing cost because of no screws and no excess/deficiency of a torque during screwing up.

Embodiment 4

A device for measuring a liquid sample of this embodiment will be described with reference to FIG. 8. In the device for measuring a liquid sample, a plurality of sensors 5 are mounted to allow multiple particular components in a liquid sample to be simultaneously measured. Each of these sensors 5 may have an elastic member or one elastic member 4 may cover all the sensors.

Embodiment 5

Figure 18:
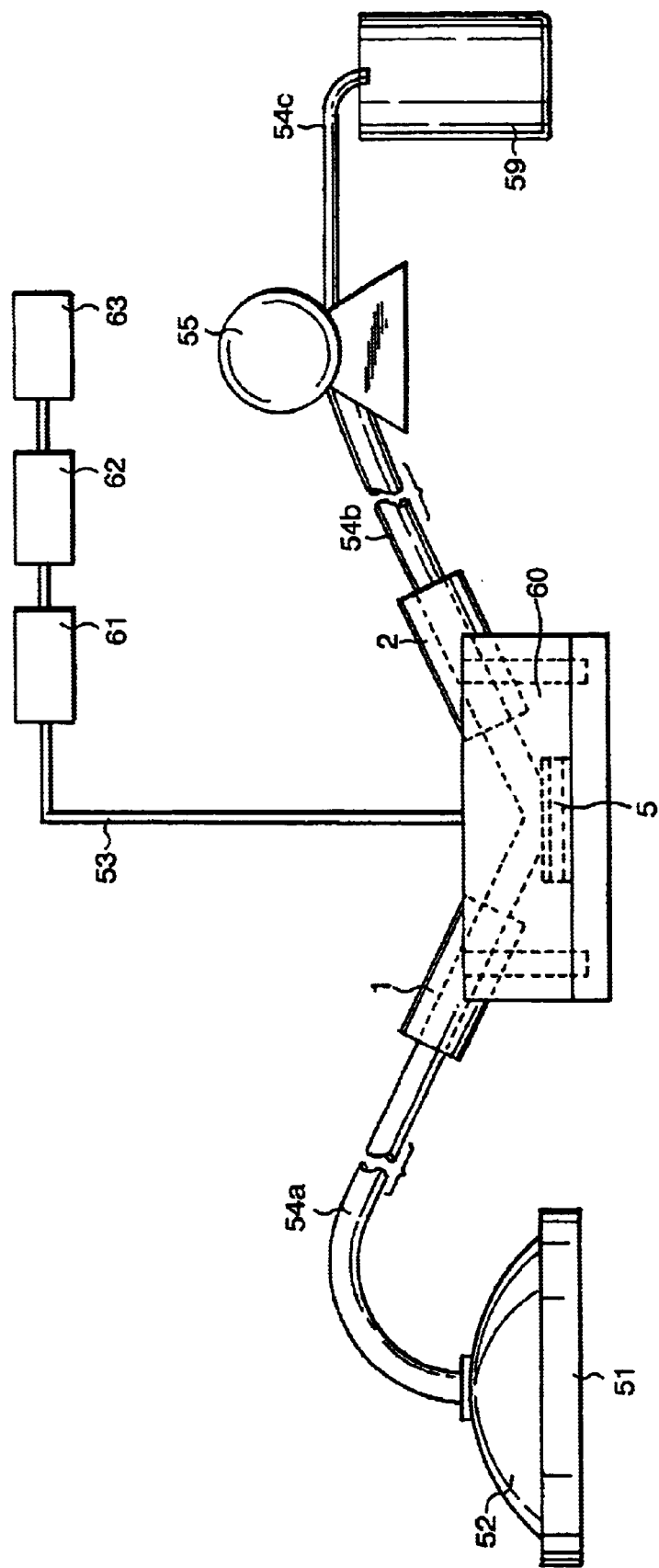
FIG. 18 shows an example of a system for measuring a liquid sample using a device for measuring a liquid sample according to this invention.

A device for measuring a liquid sample may be used, for example, with being integrated in a measuring system as illustrated in FIG. 18. In the measuring system illustrated in FIG. 18, one opening end of the liquid sample inlet channel 1 is formed in the vicinity of the sensor 5 while a tube 54a is connected with the other opening end. The end of the tube 54a is equipped with a body-fluid collection cell 52. One opening end of the liquid sample outlet channel 2 is placed in the vicinity of the sensor 5 while the other opening end is connected with a pump 55. An unshown cock is appropriately attached for allowing us to regulate a pressure within the device for measuring a liquid sample 60.

Next, there will be described a method for collecting and analyzing human body fluid using the above measuring system. Before measurement, the device for measuring a liquid sample 50 and the tubes 54a, 54b, 54c are thoroughly washed. The sensor 5 is then calibrated using a standard solution of the component to be measured. After attaching the body-fluid collection cell 52 on human skin 51, the pump 55 is activated to vacuum the insides of the device and of the channels, whereby body fluid such as interstitial fluid extracted from the skin 51 is collected in the body-fluid collection cell 52 and is passed through the tube 54a and the liquid sample inlet channel 1 to near the surface of the sensor 5. The sensor 5 comprises an electrode and an enzyme layer formed in the upper part of the electrode for obtaining a sensor output from an enzyme reaction involving the component to be measured in the enzyme layer. The output obtained in the sensor 5 is transmitted to a measuring circuit 61 via an electric wire 53 and then processed by a data processor 62 for displaying the results in a data display 63. The liquid sample which has been reached near the surface of the sensor 5 is then discharged through the liquid sample outlet channel 2 and the tube 54c to a waste tank 59.

EXAMPLES

Example 1

In this example, four types of devices for measuring a liquid sample having the structure shown in FIG. 1 were manufactured. Each device for measuring a liquid sample had one of the following sensors.

a) Glucose sensor b) Lactate sensor c) Urea sensor, d) Urate sensor.

Figure 11:
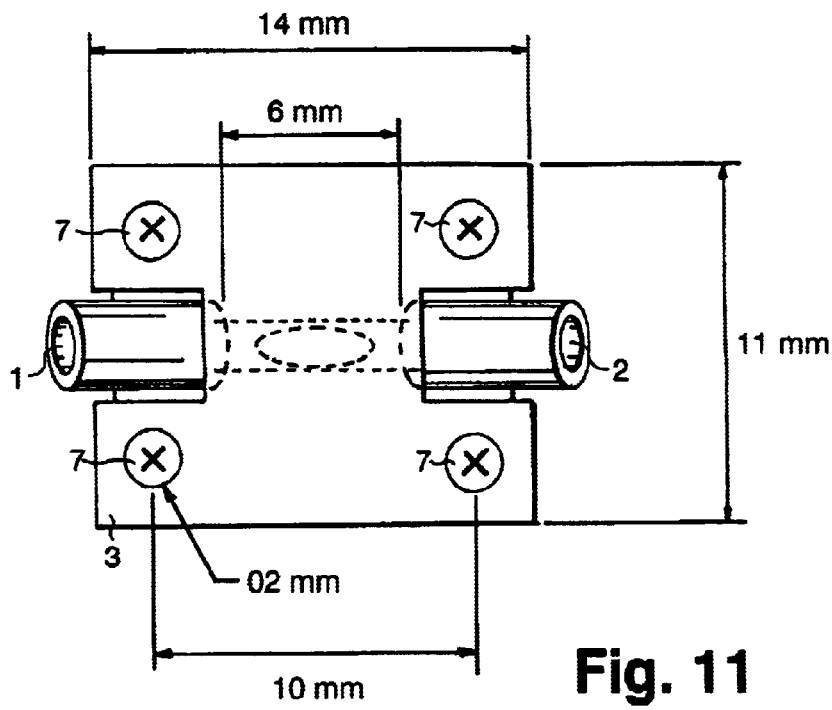
FIG. 11 shows an example of a device for measuring a liquid sample according to this invention.
Figure 12:
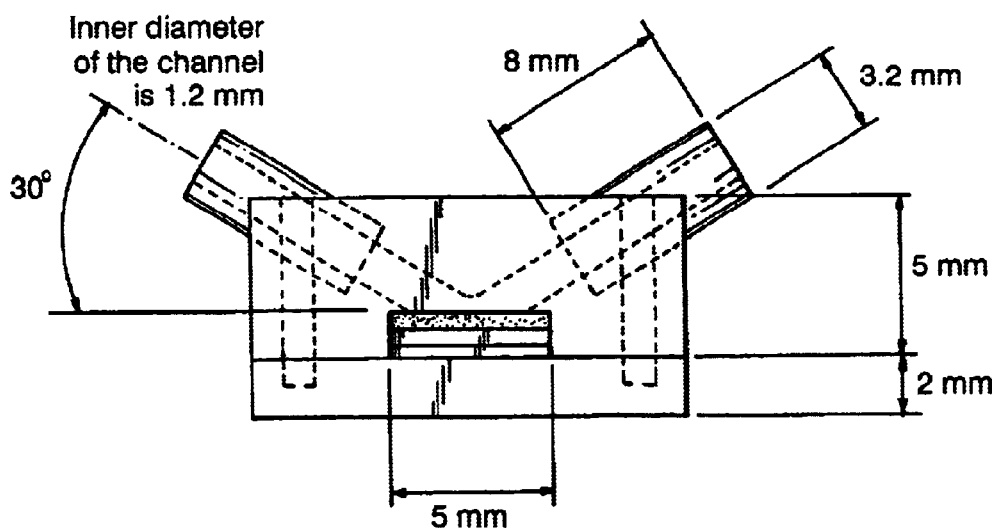
FIG. 12 shows an example of a device for measuring a liquid sample according to this invention.

Angles of the liquid sample inlet and outlet channels to the surface of the sensor 5 were 30°. Dimensions of the liquid sample inlet and outlet channels were as illustrated in FIGS. 11 and 12.

Using the above devices, a liquid-sample collection cell was attached to an upper arm of a male adult (age: 34 years, weight: 68 kg) and then glucose, lactate, urea and urate levels in body fluid (suction effusion fluid collected by vacuum suction) were determined at every 10 min for 2 hours while determining the levels of these components using a conventional laboratory test device (Trade name: Hitachi Automatic Measuring Device 7050) under the same conditions. Values thus obtained for each component were subject to regression analysis to estimate a correlation for evaluation. The results are shown in Table 1. Each measuring device used in this example, despite a simple device, exhibited higher measurement accuracy comparable to a large device for laboratory testing.

TABLE 1

| Component | Correlation coefficient (r) |
|---|---|
| Glucose | 0.971 (n = 13) |
| Lactate | 0.902 |
| Urea | 0.955 |
| Urate | 0.980 |

Example 2

Figure 8:
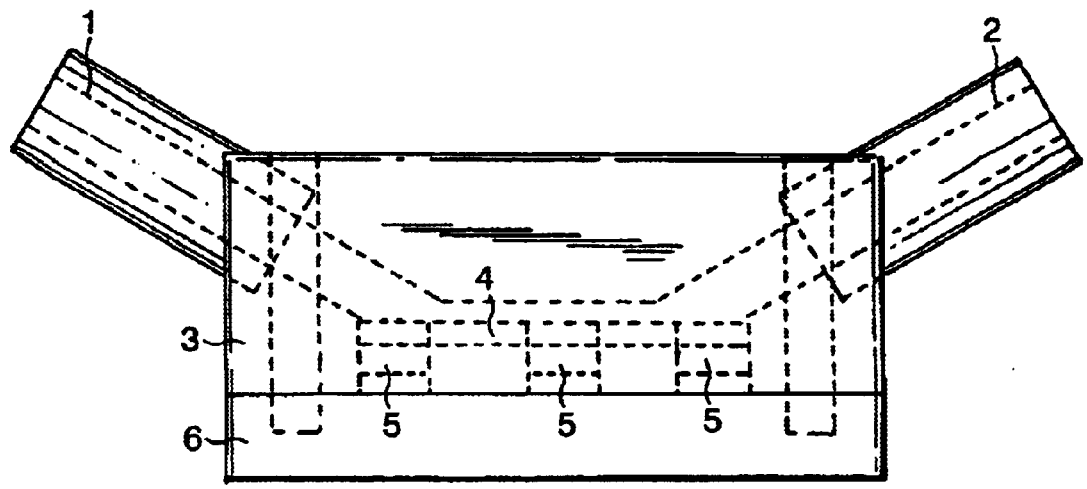
FIG. 8 shows an example of a device for measuring a liquid sample according to this invention.

A device for measuring a liquid sample comprising three types of sensors, i.e, a glucose, a lactate and an urea sensors, with the structure shown in FIG. 8 was manufactured. Angles of the liquid sample inlet and outlet channels to the surface of the sensor 5 were 30°. Dimensions of the parts except the sensor were as illustrated in FIGS. 11 and 12.

Using the above device, a liquid-sample collection cell was attached to an upper arm of a male adult (age: 34 years, weight: 68 kg) and then glucose, lactate and urea levels in body fluid (suction effusion fluid collected by vacuum suction) were determined at every 10 min for 2 hours while determining the levels of these components using a conventional laboratory test device (Trade name: Hitachi Automatic Measuring Device 7050) under the same conditions. Values thus obtained for each component were subject to regression analysis to estimate a correlation for evaluation. The results are shown in Table 2. The measuring device used in this example, despite a simple device, exhibited higher measurement accuracy comparable to a large device for laboratory testing for each component.

TABLE 2

| Component | Correlation coefficient (r) |
|---|---|
| Glucose | 0.987 (n = 13) |
| Lactate | 0.955 |
| Urea | 0.975 |

Example 3

A device for measuring a liquid sample with the structure shown in FIG. 4 was manufactured. The sensor was a glucose sensor. An antifouling layer was formed using one of the following four polymers on the whole surface of the area to be in contact with a liquid sample within the device except the surface of the sensor 5, e.g., the inner wall of the liquid sample inlet channel, the inner wall of the liquid sample outlet channel and the opening inner wall of the elastic member 4 to provide four types of devices for measuring a liquid sample. Dimensions of the parts in the device for measuring a liquid sample were as illustrated in FIGS. 11 and 12.

Materials of the Antifouling Layer
 a) 1H,1H-perfluorooctyl polymethacrylate,
 b) 1H,1H,2H,2H-perfluorodecyl polyacrylate,
 c) 1H,1H,2H,2H-perfluorodecyl polymethacrylate,
 d) 1H,1H-perfluorooctyl polyacrylate.

A device without an antifouling layer was also manufactured as a control. Angles of the liquid sample inlet and outlet channels to the surface of the sensor 5 were 30°. Using the above device, a process of injecting blood from a diabetic (male adult, age: 55 years, weight: 70 kg) at a rate of 0.1 mL/min and injecting pure water at the same rate was repeated 10 cycles, where an injection time was 15 min. At the end of the cycles, the liquid sample inlet channel, the liquid sample outlet channel and the opening inner wall of the elastic member were visually observed for adhering contaminants. Observation was conducted by counting points of visible fouling. The results are shown in Table 3. Forming the antifouling layer effectively prevented adhesion of contaminants.

TABLE 3

| Component of the antifouling layer | No. of fouling points |
|---|---|
| 1H, 1H-perfluorooctyl polymethacrylate | 0 |
| 1H, 1H, 2H, 2H-perfluorodecyl polyacrylate | 0 |
| 1H, 1H, 2H, 2H-perfluorodecyl polymethacrylate | 0 |
| 1H, 1H-perfluorooctyl polyacrylate | 0 |
| Control | 22 |

Example 4

Devices for measuring a liquid sample having the structure illustrated in FIG. 7 were manufactured, where the liquid sample inlet and outlet channels had an equal angle to the surface of the sensor 5, varying the angle from 0, 10, 20, 30, 40, 50, 60, 70 and 80°. The sensor 5 was a glucose sensor. Dimensions of the parts were as illustrated in FIGS. 11 and 12. The dimensions of the liquid sample inlet and outlet channels were as illustrated in FIGS. 11 and 12.

Using the above device, a liquid-sample collection cell was attached to an upper arm of a male adult (age: 34 years, weight: 68 kg) and then a glucose level in body fluid (suction effusion fluid collected by vacuum suction) was determined at every 10 min for 2 hours while determining the level of the component using a conventional laboratory test device (Trade name: Hitachi Automatic Measuring Device 7050) under the same conditions. Values thus obtained were subject to regression analysis to estimate a correlation for evaluation. The results are shown in Table 4. As a result, higher measurement accuracy was exhibited within the range of 10° to 60°.

TABLE 4

| Angle | Correlation coefficient (r) |
|---|---|
| 0 | 0.504 (n = 13) |
| 10 | 0.944 |
| 20 | 0.951 |
| 30 | 0.981 |
| 40 | 0.974 |
| 50 | 0.944 |
| 60 | 0.901 |
| 70 | 0.666 |
| 80 | 0.671 |

Example 5

As described in Example 4, devices for measuring a liquid sample having the structure illustrated in FIG. 4 were manufactured, where the liquid sample inlet and outlet channels had an equal angle to the surface of the sensor 5, varying the angle from 0, 10, 20, 30, 40, 50, 60, 70 and 80°. The sensor 5 was a glucose sensor. Dimensions of the parts were as illustrated in FIGS. 11 and 12. Angles of the liquid sample inlet channel etc. were different from those in FIGS. 11 and 12.

Using the above device, a liquid-sample collection cell was attached to an upper arm of a male adult (age: 34 years, weight: 68 kg) and then a glucose level in body fluid (suction effusion fluid collected by vacuum suction) was determined at every 10 min for 2 hours while measuring a time for obtaining a measured value to evaluate difference in a response speed between the sensors 5. The results are shown in Table 5. As a result, quicker response was exhibited within the range of 10° to 60° and thus a time for obtaining a measured value was reduced.

TABLE 5

| Angle | Response time (min) |
| --- | --- |
| 0 | 6.6 |
| 10 | 2.2 |
| 20 | 2.0 |
| 30 | 2.5 |
| 40 | 3.3 |
| 50 | 4.6 |
| 60 | 6.0 |
| 70 | 11.0 |
| 80 | 27.0 |

Example 6

In a device having the structure illustrated in FIG. 4, an antifouling layer was formed using 1H,1H-perfluorooctyl polymethacrylate, 1H,1H,2H,2H-perfluorodecyl polyacrylate, 1H,1H,2H,2H-perfluorodecyl polymethacrylate or 1H,1H-perfluorooctyl polyacrylate. A device without an antifouling layer was also manufactured as a control. Angles of the liquid sample inlet and outlet channels to the surface of the sensor 5 were 30°. The sensor 5 was a glucose sensor. Dimensions of parts in the device for measuring a liquid sample were as illustrated in FIGS. 11 and 12.

A process of injecting blood from a diabetic (male adult, age: 55 years, weight: 70 kg) at a rate of 0.1 mL/min and injecting pure water at the same rate was repeated 10 cycles, where an injection time was 15 min. At the end of the cycles, a time for obtaining a measured value was measured to evaluate difference in a response speed between the sensors 5. Evaluation was based on an average of 10 measured values. The results are shown in Table 6. As a result, antifouling treatment improved a response speed to reduce a time for obtaining a measured value.

TABLE 6

| Component of the antifouling layer | Response time (min) |
| --- | --- |
| 1H, 1H-perfluorooctyl polymethacrylate | 2.0 |
| 1H, 1H, 2H, 2H-perfluorodecyl polyacrylate | 2.2 |
| 1H, 1H, 2H, 2H-perfluorodecyl polymethacrylate | 2.1 |
| 1H, 1H-perfluorooctyl polyacrylate | 2.1 |
| Control | 3.2 |

Example 7

Devices for measuring a liquid sample having the structure illustrated in FIG. 4 were manufactured, where the liquid sample inlet and outlet channels had an equal angle to the surface of the sensor 5, varying the angle from 0, 30 and 60°. The sensor 5 was a glucose sensor.

Using the device, a time for replacing the sensor 5 was measured. Table 7 shows the results obtained by calculating an average of 10 measured values. It can be seen that in the device for measuring a liquid sample of this example comprising an elastic member, the sensor can be mounted in a particularly short time at an angle of 30° or 60° although the sensor may be mounted in a short time for any angle because alignment of the sensor surface and the upper case 3 is particularly easy.

TABLE 7

| Angle | Mounting time (min) |
| --- | --- |
| 0 | 2.5 |
| 30 | 2.0 |
| 60 | 2.1 |

Example 8

Figure 9:
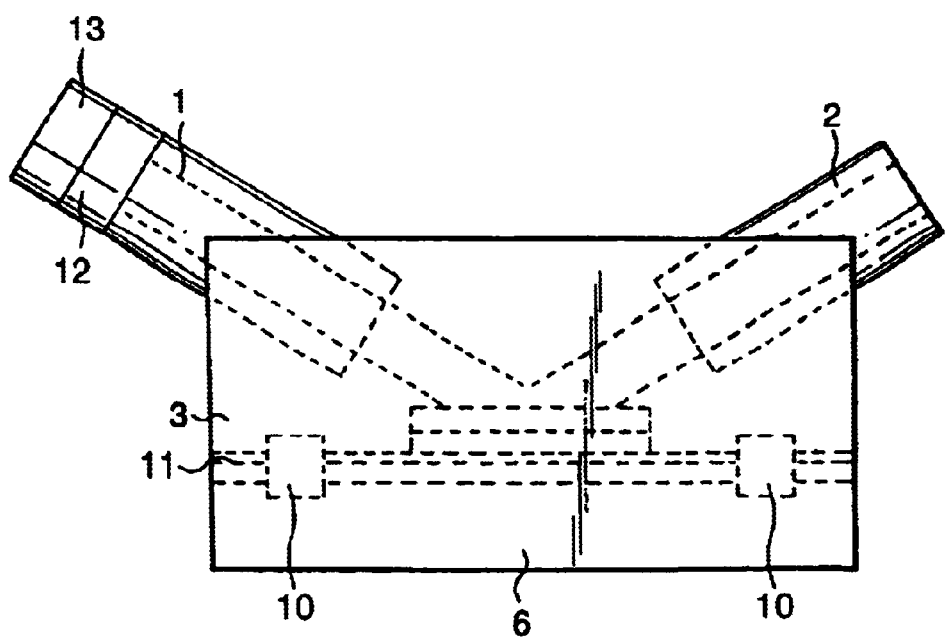
FIG. 9 shows an example of a device for measuring a liquid sample according to this invention.
Figure 10:
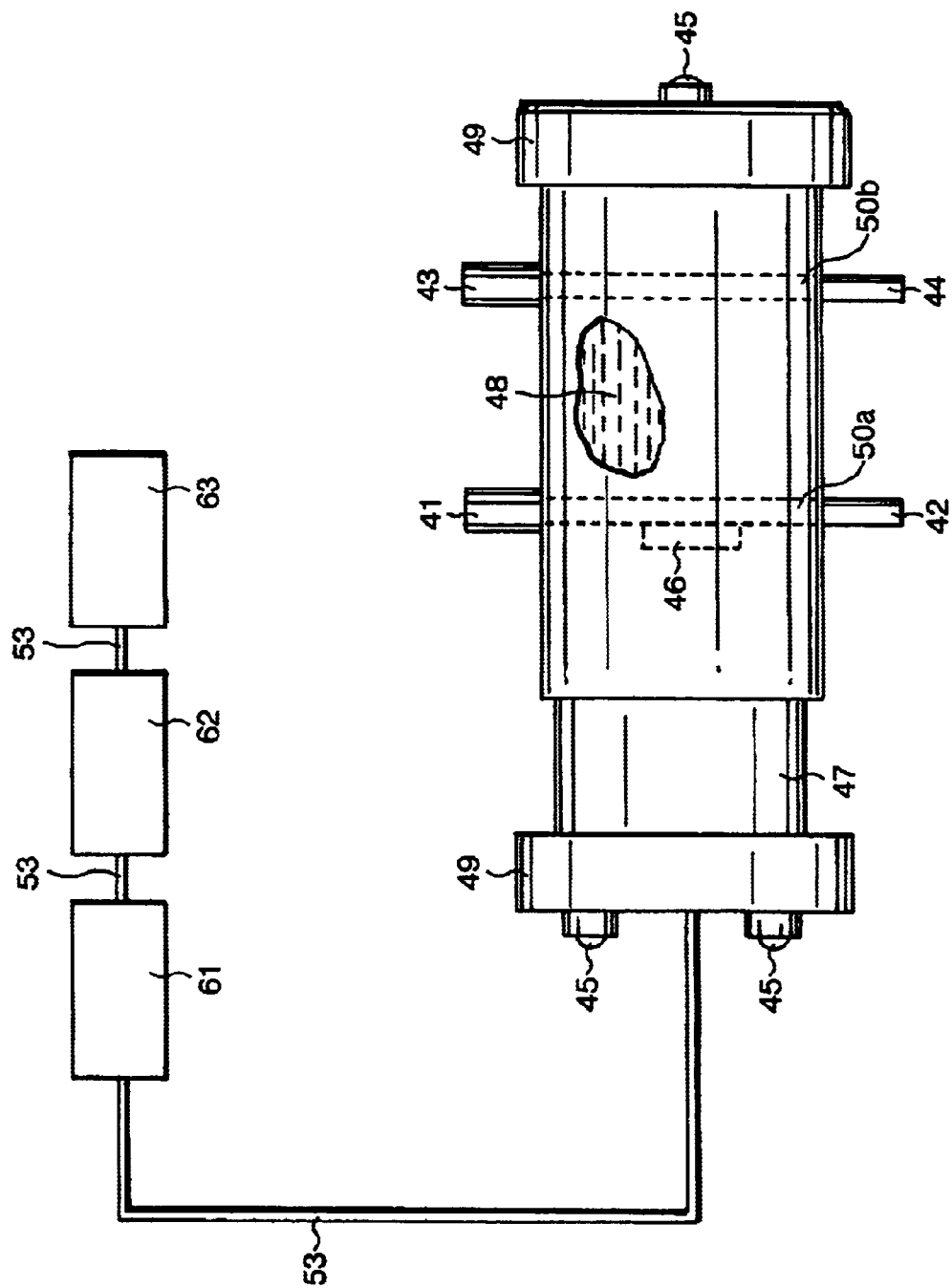
FIG. 10 shows an example of a conventional device for measuring a liquid sample.

A device for measuring a liquid sample having the structure illustrated in FIG. 9 was manufactured. The sensor 5 was a glucose sensor. The sensor 5 consisted of a working, a counter and a reference electrodes, and the counter and the reference electrodes were placed at the inlet of the liquid sample inlet channel. An angle of the liquid sample inlet or outlet channel to the horizontal plane was 30°. Dimensions of the parts in the device for measuring a liquid sample were as illustrated in FIGS. 11 and 12. Dimensions of the liquid sample inlet and outlet channels were as illustrated in FIGS. 11 and 12.

Using the above device, a liquid-sample collection cell was attached to an upper arm of a male adult (age: 34 years, weight: 68 kg) while determining the level of the component using a conventional laboratory test device (Trade name: Hitachi Automatic Measuring Device 7050) under the same conditions. Values thus obtained for the component were subject to regression analysis to estimate a correlation for evaluation. The results are shown in Table 8. As a result, it is confirmed that improved measurement accuracy can be achieved even when mounting the working electrode distant from the counter or reference electrode.

TABLE 8

| Component | Correlation coefficient (r) |
| --- | --- |
| Glucose | 0.908 (n = 13) |

Example 9

In this example, there will be an example of measurement of a liquid sample using a measuring system shown in FIG. 18.

A device for measuring a liquid sample used in this example has a structure shown in FIG. 1 and the sensor 5 was a glucose sensor. An angle of the liquid sample inlet or outlet channel to the surface of the sensor 5 was 30°. Dimensions of the liquid sample inlet and outlet channels were as illustrated in FIGS. 11 and 12.

The glucose sensor was manufactured as follows. On a quartz substrate with a size of 8 mm×4.5 mm were formed a working electrode (area: 2 mm$^2$), a counter electrode (area: 0.5 mm$^2$) and a reference electrode consisting of silver/silver chloride (area: 0.5 mm$^2$). Then, over the whole surface was applied by spin coating a 1 v/v % solution of γ-aminopropyltriethoxysilane to form a binding layer. Then, on the surface was applied by spin coating a 22.5 w/v % solution of albumin containing 56.6 U/μL glucose oxidase and 1 v/v % glutaraldehyde to form an immobilized enzyme layer. On the layer was applied by spin coating a 1.7 v/v % solution of a polyfluoroalcohol ester of methacrylic acid resin to form a permeation restricting layer. The conditions of spin coating were 3000 rpm and 30 sec. The molecular weight of the polyfluoroalcohol ester of methacrylic acid resin was about 7000.

The electrodes and the flexible substrate were interconnected via a wire bonding while the flexible substrate and the electrochemical-measurement circuit was interconnected via a pin-jack type electric wire. The electrochemical-measurement circuit was a potentiostat HOKUTODENKO POTENTIOSTAT/GALVANOSTAT HA150G (Hokuto Denko). A data processor was a personal computer PC-9821RaII23 (Nippon Denki). The electrochemical-measurement circuit, the data processor and the data display were interconnected via a pin-jack type electric wire.

On the device for measuring a liquid sample were mounted several elements such as a pump, a tube and a body-fluid collection cell to provide a system for measuring a liquid sample having the structure illustrated in FIG. 18.

There will be described a method for measuring a liquid sample using this system for measuring a liquid sample.

A tube was connected to the liquid sample inlet channel, through which was then injected a 1 mM buffer of TES (N-tris(hydroxyl)methyl-2-aminoethanesulfonic acid) containing 150 mM sodium chloride, pH 7, to wet the sensor 5. Then, the device was turned on and 0.7 V was applied to the working electrode in relation to the reference electrode.

Figure 13:
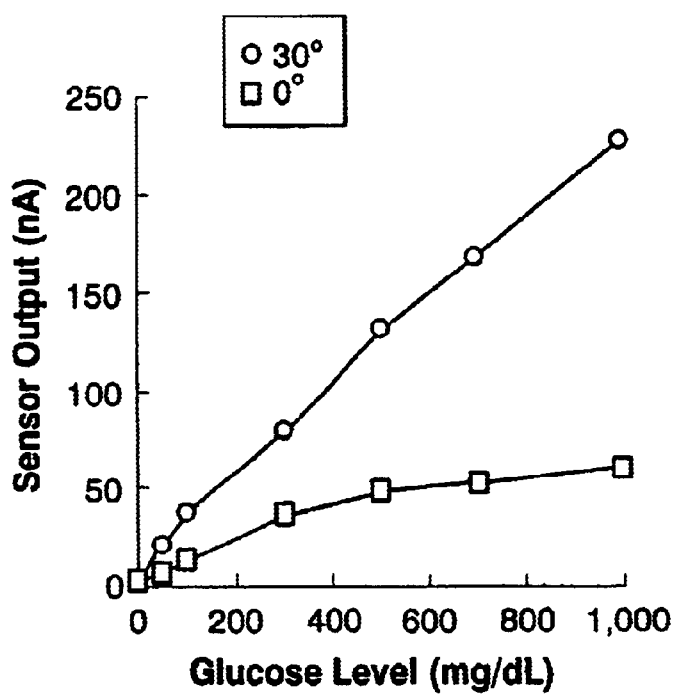
FIG. 13 is a graph illustrating a relationship between a glucose level and a sensor output.

Then, the sensor 5 was calibrated. To the voltage-applied sensor 5 were sequentially injected 50, 100, 300, 500, 700 and 1000 mg/dL glucose solutions from the tube connected to the liquid sample inlet channel to determine a sensor output (current value). From the liquid sample outlet channel, a waste after determination was discharged. An injection rate was 100 μL/min. A calibration curve was plotted for 0 to 1000 mg/dL glucose. The plotted calibration curve for glucose is shown in FIG. 13 (white circles in the figure). The calibration curve obtained was highly linear and a higher sensor output was obtained.

Figure 14:
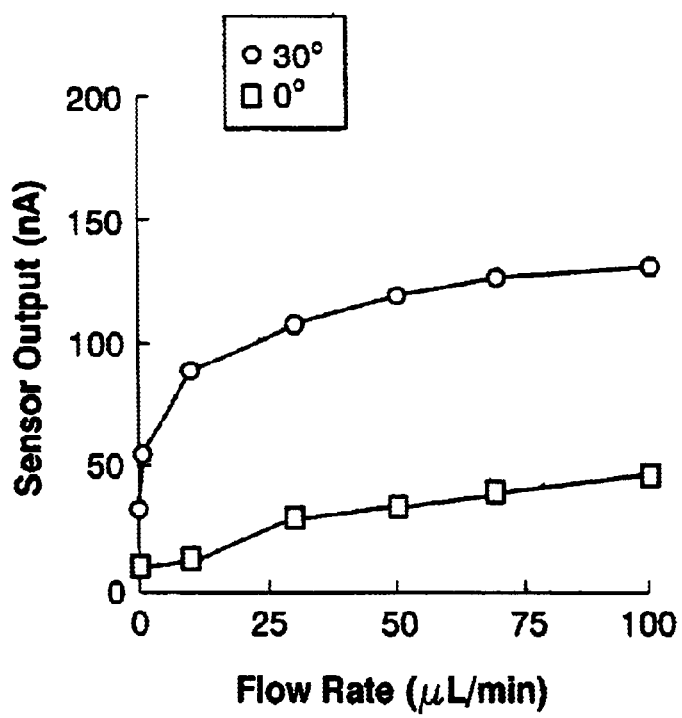
FIG. 14 is a graph illustrating a flow rate of a liquid sample and a sensor output.

Then, the buffer was again injected and the system was allowed to stand until it became steady state. Then, while varying an injection rate (flow rate) from 0.5, 1, 10, 30, 50, 70 to 100 μL/min, sensor outputs of 500 mg/dL glucose were determined for these injection rates. A relationship between a flow rate and a sensor output is shown in FIG. 14 (white circles in the figure). The results in this figure indicate that a flow rate of 50 μL/min or more may minimize flow-rate dependency of a sensor output and thus measurement within the range may provide stable measured values. Actually, it was confirmed that a calibration curve obtained exhibited good linearity within the range of 50 μL or more. It indicates that when determining a glucose level using a device for measuring a liquid sample of this example, a flow rate of 50 μL or more may provide more accurate and stable measurement results.

Next, a device for measuring a liquid sample was manufactured and measurement was conducted as described above except that an angle of the liquid sample inlet or outlet channel to the surface of the sensor 5 was 0°. A plotted calibration curve for glucose is shown in FIG. 13 and effect of an injection rate on a sensor output is shown in FIG. 14 (white squares in this figure).

As seen from FIG. 13, it was observed that when the angle was 0°, the calibration curve is insufficiently linear and has a smaller slope, leading to increase of an error in glucose level determination. As seen from FIG. 14, a sensor output was low in any flow rate, indicating inadequate measurement accuracy.

As described above, a device for measuring a liquid sample according to this invention employs a configuration that a liquid sample inlet channel is placed at an angle to a sensor surface and one opening end of the liquid sample inlet channel is placed in the vicinity of the sensor surface, whereby a flow condition of the liquid sample suitable to measurement near the sensor surface may be achieved, resulting in excellent measurement accuracy, stable measurement sensitivity and quick response.

In a device for measuring a liquid sample according to this invention, since the sensor is removable from the upper case, a worn sensor may be quickly replaced and cleaning of the inside of the device may be easy. Since the sensor, the upper case and the lower case may be separately manufactured, the upper and the lower cases may be produced in a large scale by, for example, injection molding and degree of freedom may be increased in designing a shape of the sensor.

A device for measuring a liquid sample according to this invention may have a configuration that an elastic member having an opening is placed between the upper case and the sensor surface to prevent formation of a dead space and leakage of a liquid and to significantly minimize influence of misalignment during mounting the sensor on the case. Since formation of a dead space can be effectively prevented, accurate measurement may be conducted even with a small amount of sample.

A device for measuring a liquid sample according to this invention may have a configuration that an antifouling layer is formed on the inner wall of the liquid sample inlet channel and the inner wall of the liquid sample outlet channel so that sensitivity reduction may be minimized during repeated or continuous measurement and good measurement accuracy and measured-value stability may be achieved. Forming an antifouling layer may further accelerate a response speed of the sensor.

What is claimed is:

1. A device for measuring a liquid sample comprising:
   a sensor for measuring a component in the liquid sample,
   an upper part comprising a liquid sample inlet channel having an end with an opening for feeding the liquid sample onto a surface of the sensor and a liquid sample outlet channel having an end with an opening for discharging the liquid sample from the sensor surface, and
   a lower part;
   wherein
   the upper and lower parts vertically sandwich the sensor, the sensor having an electrode and an enzyme layer in an upper part of the electrode, the liquid sample inlet channel being placed at an angle, selected in the range of one degree to eighty degrees, to the sensor surface,
   the end opening of the liquid sample inlet channel being placed at a predefined distance from the sensor surface, and
   the predefined distance between the sensor surface and the end opening of the liquid sample inlet channel being two fold or less of an inner diameter of the liquid sample inlet channel.

2. The device for measuring a liquid sample as claimed in claim 1, wherein
   the liquid sample outlet channel being placed at an angle to the sensor surface, the end opening of the liquid sample outlet channel being placed at a predefined distance from the sensor surface, and the predefined distance of the end opening of the liquid sample outlet channel being the same as the predefined distance of the end opening of the liquid sample inlet channel.

3. The device for measuring a liquid sample as claimed in claim 1 wherein the liquid sample inlet and outlet channels are formed substantially in the same plane.

4. The device for measuring a liquid sample as claimed in claim 1 wherein an antifouling layer is formed on the inner surfaces of the liquid sample inlet and outlet channels.

5. The device for measuring a liquid sample as claimed in claim 4 wherein the antifouling layer comprises a fluoroalcohol ester of a polycarboxylic acid.

6. The device for measuring a liquid sample as claimed in claim 2 wherein the angle of the liquid sample outlet channel to the sensor surface is selected in the range of 1 degree to 80 degrees.

7. A device for measuring a liquid sample comprising:

a sensor for measuring a component in the liquid sample, an upper part comprising a liquid sample inlet channel having an end with an opening for feeding the liquid sample onto a surface of the sensor and a liquid sample outlet channel having an end with an opening for discharging the liquid sample from the sensor surface, and a lower part;

wherein, the upper and lower parts vertically sandwich the sensor, the sensor having an electrode and an enzyme layer in an upper part of the electrode and being removable from the upper the liquid sample inlet channel being placed at an angle, selected in the range of one degree to eighty degrees, to the sensor surface, the end opening of the liquid sample inlet channel being placed at a predefined distance from the sensor surface, and the predefined distance between the sensor surface and the end opening of the liquid sample inlet channel being two fold or less of an inner diameter of the liquid sample inlet channel.

8. The device for measuring a liquid sample as claimed in claim 7 wherein a film-shaped elastic member having an opening is placed between the upper part and the sensor surface;

the opening interconnects between the end opening of the liquid sample inlet channel and the sensor, and between the end opening of the liquid sample outlet channel and the sensor, and a part of the sensor surface is in contact with the liquid sample via the opening.

9. The device for measuring a liquid sample as claimed in claim 7 wherein the end opening of the liquid sample inlet channel and the end opening of the liquid sample outlet channel together form a common end opening.

10. The device for measuring a liquid sample as claimed in claim 9 wherein a periphery of the common end opening is formed in a lower surface of the upper part and is outer from that of the opening in a film-shaped elastic member.

11. The device for measuring a liquid sample as claimed in claim 7 wherein the liquid sample outlet channel being placed at an angle to the sensor surface, the end opening of the liquid sample outlet channel being placed at a predefined distance from the sensor surface, and the predefined distance of the end opening of the liquid sample outlet channel being the same as the predefined distance of the end opening of the liquid sample inlet channel.

12. The device for measuring a liquid sample as claimed in claim 7 wherein the liquid sample inlet and outlet channels are formed substantially in the same plane.

13. The device for measuring a liquid sample as claimed in claim 7 wherein an antifouling layer is formed on the inner surfaces of the liquid sample inlet and outlet channels.

14. The device for measuring a liquid sample as claimed in claim 13 wherein the antifouling layer comprises a fluoroalcohol ester of a polycarboxylic acid.

15. The device for measuring a liquid sample as claimed in claim 8 wherein the film-shaped elastic member is made of a film of a silicone resin or fluororesin having a thickness of 0.1 $\mu$m to 1 mm.

16. The device for measuring a liquid sample as claimed in claim 11 wherein the angle of the liquid sample outlet channel to the sensor surface is selected in the range of 1 degree to 80 degrees.

17. A device for measuring a liquid sample comprising:

an amperometric detection electrochemical sensor for measuring a component in the liquid sample comprising a working electrode, a counter electrode and a reference electrode, an upper part comprising a liquid sample inlet channel having an end with an opening for feeding the liquid sample onto a surface of the working electrode of the sensor and a liquid sample outlet channel having an end with an opening for discharging the liquid sample from the sensor surface and a lower part;

wherein the upper and lower parts vertically sandwich the sensor, the working electrode of the sensor having and an enzyme layer in an upper part of the electrode, the liquid sample inlet channel being placed at an angle, selected in the range of one degree to eighty degrees, to the working electrode surface of the sensor, the end opening of the liquid sample inlet channel being placed at a predefined distance from the working electrode surface of the sensor, and the predefined distance between the working electrode surface and the end opening of the liquid sample inlet channel being two fold or less of an inner diameter of the liquid sample inlet channel.

* * * * *